United States Patent [19]

Oka

[11] Patent Number: 4,559,361
[45] Date of Patent: Dec. 17, 1985

[54] NAPHTHALENECARBOXAMIDES, THEIR PRODUCTION AND USE

[75] Inventor: Yoshikazu Oka, Kawanishi, Japan

[73] Assignee: Senju Pharmaceutical Co., Ltd., Osaka, Japan

[21] Appl. No.: 538,805

[22] Filed: Oct. 5, 1983

[30] Foreign Application Priority Data

Oct. 15, 1982 [JP] Japan ................................. 57-181948

[51] Int. Cl.⁴ .................. C07C 103/28; A61K 31/165
[52] U.S. Cl. .................................... 514/620; 564/164; 564/167; 514/619
[58] Field of Search ................ 564/167, 164; 424/324; 514/619, 620

[56] References Cited

U.S. PATENT DOCUMENTS

| | | | |
|---|---|---|---|
| 2,029,509 | 2/1936 | Sexton | 564/167 |
| 4,035,512 | 7/1977 | Sugihara et al. | 424/330 |
| 4,410,519 | 10/1983 | Seiler et al. | 564/167 X |
| 4,442,126 | 4/1984 | Beeley et al. | 424/324 |
| 4,448,990 | 5/1984 | Bach et al. | 564/167 |
| 4,473,586 | 9/1984 | Debernardis et al. | 424/324 X |

*Primary Examiner*—Thomas A. Waltz
*Attorney, Agent, or Firm*—Wenderoth, Lind & Ponack

[57] ABSTRACT

Novel compounds of the formula:

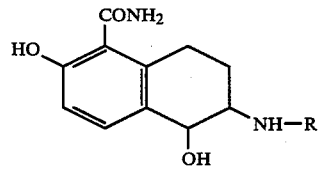

wherein R is phenyl-$C_{1-6}$ alkyl, and salts thereof, have intraocular pressure depressant action.

3 Claims, No Drawings

NAPHTHALENECARBOXAMIDES, THEIR PRODUCTION AND USE

This invention relates to novel naphthalenecarboxamide compounds having an excellent pharmacological action.

More particularly, this invention provides compounds of the formula:

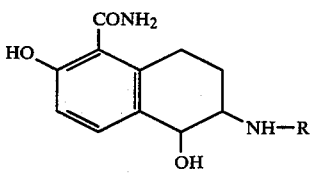

wherein R is phenyl-$C_{1-6}$ alkyl and salts thereof, which have intraocular pressure depressant action.

U.S. Pat. No. 4,035,512 describes the broad concept of tetralol compounds which encompasses the compound of the formula [I] among other compounds. However, this patent does not concretely disclose the compound [I] nor does it contain any statement suggesting the utility of such compounds in the field of ophthalmology.

The present invention has been accomplished as the result of the present inventor's intensive research directed to the ophthalmologic application of various salicyclic acid derivatives.

Referring to the formula [I], phenyl-$C_{1-6}$ alkyl for R is exemplified by benzyl, phenethyl, 3-phenylpropyl, α-methylbenzyl, α-methylphenethyl, 1-methyl-3-phenylpropyl, 2-methyl-3-phenylpropyl, 1-methyl-4-phenylbutyl, 3-phenylpentyl, 6-phenylhexyl and 1,1-dimethyl-3-phenylpropyl. Most desirable is 1-methyl-3-phenylpropyl.

The compound of the formula [I] can be produced, for example by condensing under reducing conditions a compound of the formula:

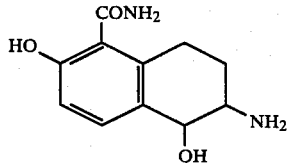

with a compound of the formula

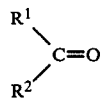

wherein $R^1$ is phenyl-$C_{1-5}$ alkyl or phenyl, $R^2$ is hydrogen or $C_{1-5}$ alkyl and the group represented by

corresponds to R of the formula [I]. Alternatively, the compound of formula [I] can be produced by condensing under reducing conditions a compound of the formula:

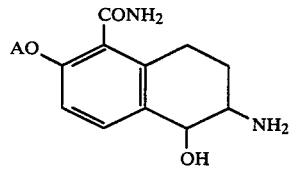

wherein A is a hydroxy-protecting group selected from the group consisting of lower alkyl and aralkyl, with the compound of the formula [III] to give a compound of the formula

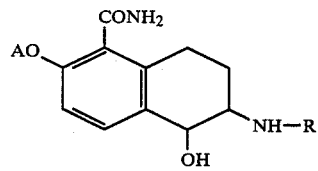

wherein A and R are as defined above, and subjecting the thus obtained compound of the formula [V] to a deprotecting reaction to remove the hydroxy-protecting group.

Referring to the above formulas, phenyl-$C_{1-5}$ alkyl for $R^1$ is exemplified by benzyl, phenethyl, 3-phenylpropyl, 4-phenylbutyl, α-methylbenzyl, α-methylphenethyl and 5-phenylpentyl. $C_{1-5}$ alkyl $R^2$ is exemplified by methyl, ethyl, propyl, isopropyl, butyl and the like. The lower alkyl A is exemplified by methyl, ethyl, propyl, isopropyl, butyl, etc. and the aralkyl A is exemplified by benzyl, phenethyl, 3-phenylpropyl and so on.

The above reaction between [I] and [III] and that between [IV] and [III] are carried out generally by reducing both compounds in water or an organic solvent (for example, methanol, ethanol, dioxane, ethyl acetate, etc.) or a mixture thereof. This reduction reaction may for example be catalytic reduction with the aid of a catalyst such as platinum, palladium, Raney nickel, etc.; reduction using a metal hydrogen compound such as lithium aluminum hydride, lithium borohydride, lithium cyanoborohydride, sodium borohydride, sodium cyanoborohydride, etc.; reduction using sodium metal, magnesium metal or the like and an alcohol; reduction using zinc dust and a base; or reduction using a metal such as iron, zinc or the like and an acid such as hydrochloric acid or acetic acid. Aside from these reduction reactions, any other reduction method can be employed. While the reaction temperature varies with different reduction methods, it is generally advantageous to conduct the reduction at a temperature of about −20° C. to about 100° C. This reaction can be successfully conducted at atmospheric pressure but, if necessary, it may be conducted at elevated or reduced pressure.

The above-mentioned deprotection reaction for [V] may be carried out in any known manner. For example, solvolysis, hydrogenolysis, etc. can be utilized with advantage. More particularly, there may preferably be employed such reactions as (1) catalytic reduction with the aid of a catalyst such as platinum, palladium, rhodium, Raney nickel, etc.; (2) reduction using liquid ammonia or alcohol (e.g. ethanol, butanol, etc.) and a metal (e.g. sodium metal, potassium metal, etc.); (3) reaction with a Lewis acid such as aluminum chloride, aluminum bromide, zinc chloride, magnesium iodide, iron chloride, boron trichloride, boron trifluoride, etc.; (4) reaction with an acid such as a hydrogen halide (e.g. hydrogen fluoride, 48% hydrobromic acid, hydrogen fluoride-acetic acid, hydrochloric acid, hydrogen iodide, etc.), sulfuric acid, nitric acid, phosphoric acid, perchloric acid, boric acid, etc. or a solution thereof in water, alcohol or the like; (5) reaction with an organic acid such as trifluoroacetic acid, acetic acid, oxalic acid, p-toluenesulfonic acid, formic acid, etc. or an aqueous solution thereof; (6) reaction with an inorganic base such as sodium hydroxide, potassium hydroxide, barium hydroxide, potassium carbonate, sodium hydrogen carbonate, aqueous ammonia, hydrazine hydrate, etc., or an organic base such as pyridine hydrochloride, tetramethylammonium hydroxide, collidine-lithium iodide, etc. The reaction temperature varies with the kind of reaction but generally speaking, the range of about −40° C. to about 150° C. is desirable. While these reactions are generally conducted at atmospheric pressure, they may be carried out at reduced or elevated pressure.

The resulting contemplated compound [I] can be isolated by the conventional isolation procedures such as extraction, concentration, neutralization, filtration, recrystallization, column chromatography, thin layer chromatography, etc.

Since the compound of the formula [I] contains an asymmetric carbon within its molecule, it exists as several optical isomers. All of these individual isomers as well as a racemic mixture thereof fall within the scope of the present invention. While the compound of formula [I] is generally obtained as a mixture of isomers, it can be separated into individual component isomers by the per se conventional separation procedures such as the method of producing a salt with an optically active base (e.g. cinchonine, cinchonidine, quinine, quinidine, etc.), various chromatographic procedures, fractional crystallization, etc.

The contemplated compound [I] of this invention may also be isolated after it has been converted to salts, especially to physiologically acceptable salts such as acid addition salts and alkaline metal salts in the conventional manner; for example, an inorganic acid salt (such as hydrochloride, hydrobromide, sulfate, etc.), an organic acid salt (such as maleate, fumarate, tartrate, toluenesulfonate, naphthalenesulfonate, methanesulfonate, etc.), and a metal salt (such as sodium salt, potassium salt, etc.)

The compound of the present invention exhibits intraocular pressure depressant activity in mammalian animals inclusive of man, and is low in toxicity. Therefore, it is of value as a drug for the treatment of glaucoma, for instance. The administration routes include oral and parenteral but it is generally preferable to use the compound locally as an ophthalmic solution. In ophthalmological application, it is desirably used as a 0.01 to 1% (w/v) ophthalmic solution and administered at a frequency of 3 to 5 times daily, one to a few drops per dose.

An ophthalmic solution containing the compound [I] or a salt thereof may be prepared by per se conventional techniques using a suitable pharmaceutically acceptable carrier, vehicle or diluent.

The ophthalmic solution may, if desired, contain other and conventional ophthalmic ingredients such as boric acid, preservatives, salts, antibiotics, vitamins, amino acids and so forth.

The starting compound [II] for use in the practice of the present invention can be prepared, for example by the following reactions:

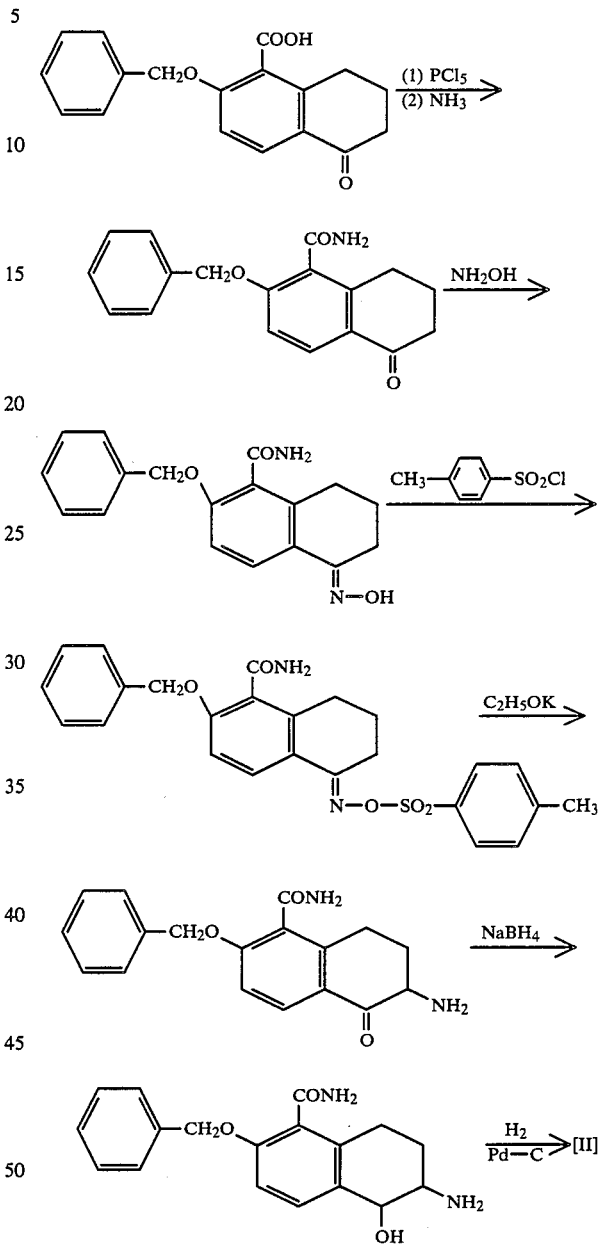

The following reference, working and preparation examples are given to illustrate the present invention in further detail and should by no means be construed as limiting the scope of the invention.

REFERENCE EXAMPLE 1

In 200 ml of benzene was dissolved 27 g of 2-benzyloxy-5-oxo-5,6,7-8-tetrahydro-1-naphthoic acid and after addition of 22.7 g of phosphorus pentachloride, the solution was refluxed for 1 hour. The solvent was then distilled off and the residue was dissolved in 200 ml of dioxane. Ammonia gas was bubbled through the dioxane solution at room temperature for 1 hour, after which the solution was poured into 500 ml of water and extracted with 300 ml of ethyl acetate. The extract was washed with water, dried and distilled to give 20 g of 2-benzyloxy-5-oxo-5,6,7,8-tetrahydro-1-naphthalenecarboxamide. Recrystallization from ethyl acetate gave crystals melting at 192°–194° C.

REFERENCE EXAMPLE 2

To a mixture of 20 ml of methanol and 2 ml of water were added 3 g of 2-benzyloxy-5-oxo-5,6,7,8-tetrahydro-1-naphthalenecarboxamide, 2 g of potassium carbonate and 2.8 g of hydroxylamine hydrochloride, and the solution was refluxed under stirring for 3 hours. After cooling, the reaction mixture was poured into 50 ml of water and the crystals separating out were collected and recrystallized from 50% methanol, whereby 3 g of 2-benzyloxy-5-hydroxyimino-5,6,7,8-tetrahydro-1-naphthalenecarboxamide, m.p. 244°–246° C., was obtained.

REFERENCE EXAMPLE 3

In 10 ml of pyridine was dissolved 3 g of 2-benzyloxy-5-hydroxyimino-5,6,7,8-tetrahydro-1-naphthalenecarboxamide and, then, 4 g of p-toluenesulfonyl chloride was added in small portions under ice-cooling. The mixture was stirred at 5° C. for 30 minutes and, further, at room temperature for 1 hour. The reaction mixture was poured into 100 ml of ice-water and the crystals separating out were collected by filtration and recrystallized from methanol. The above procedure yielded 2.8 g of 2-benzyloxy-5-p-toluenesulfonyloxyimino-5,6,7,8-tetrahydro-1-naphthalenearboxamide as colorless crystals, m.p. 149°–151° C.

REFERENCE EXAMPLE 4

A solution of 15 g of 2-benzyloxy-5-p-toluenesulfonyloxyimino-5,6,7,8-tetrahydro-1-naphthalenecarboxamide in 300 ml of benzene was ice-cooled and a solution of potassium ethoxide prepared from an equivalent of potassium metal in anhydrous methanol was added under a nitrogen gas stream. The mixture was stirred under ice-cooling for 5 hours and, then, allowed to stand in a refrigerator for 1 week. The precipitates were filtered off and 25 ml of concentrated hydrochloric acid was added to the filtrate. The crystals separating out were collected by filtration and recrystallized from 200 ml of ethanol. The procedure yielded 7 g of 6-amino-2-benzyloxy-5-oxo-5,6,7,8-tetrahydro-1-naphthalenecarboxamide hydrochloride melting at 227°–230° C.

REFERENCE EXAMPLE 5

In 50 ml of methanol was dissolved 2 g of 6-amino-2-benzyloxy-5-oxo-5,6,7,8-tetrahydro-1-naphthalenecarboxamide followed by addition of 2 g of sodium borohydride at room temperature. The mixture was stirred for 30 minutes, after which it was diluted with 300 ml of water and extracted three times with 50 ml portions of chloroform. The extract was washed with water, dried and distilled, and the residue was dissolved in 50 ml of ethyl ether, followed by addition of 5 ml of 20% ethanolic hydrochloric acid. The resulting crystals were recrystallized from methanol-ethylether to give 1.5 g of trans-6-amino-2-benzyloxy-5-hydroxy-5,6,7,8-tetrahydro-1-naphthalenecarboxamide hydrochloride, m.p. 220°–222° C.

REFERENCE EXAMPLE 6

In 30 ml of methanol was dissolved 1 g of trans-6-amino-2-benzyloxy-5-hydroxy-5,6,7,8-tetrahydro-1-naphthalenecarboxamide hydrochloride, followed by addition of 5 g of benzylacetone. Then, under ice-cooling, 1 g of sodium cyanoborohydride was added and the mixture was allowed to stand at room temperature overnight. The reaction mixture was diluted with 300 ml of water and extracted 3 times with 30 ml of $CHCl_3$. The $CHCl_3$ layers were combined, washed with water, dried and concentrated under reduced pressure. The residue was dissolved in 50 ml of ethyl ether, followed by addition of 5 ml of 20% ethanolic hydrochloric acid, whereby 0.84 g of trans-2-benzyloxy-5-hydroxy-6-(1-methyl-3-phenylpropylamino)-5,6,7,8-tetrahydro-1-naphthalenecarboxamide hydrochloride was obtained as colorless crystals, m.p. 215°–218° C.

Elemental analysis: $C_{28}H_{32}N_2O_3 \cdot HCl$. Calcd.: C, 69.91; H, 6.91; N, 5.82. Found: C, 70.11; H, 7.15; N, 5.69.

NMR spectrum, $\delta(d_6\text{-DMSO})$: 4.75(1H, d, J=9 Hz, $C_1$—H).

EXAMPLE

In 50 ml of methanol was dissolved 1 g of trans-2-benzyloxy-5-hydroxy-6-(1-methyl-3-phenylpropylamino)-5,6,7,8-tetrahydro-1-naphthalenecarboxamide hydrochloride and catalytic reduction was carried out in the presence of 1 g of 10% palladium-on-carbon at atmospheric temperature and pressure. After the absorption of hydrogen was completed, the catalyst was filtered off and the filtrate was distilled under reduced pressure. To the residue was added 50 ml of ethyl ether, whereby 0.56 g of trans-2,5-dihydroxy-6-(1-methyl-3-phenylpropylamino)-5,6,7,8-tetrahydro-1-naphthalenecarboxamide hydrochloride was obtained as colorless powder.

Elemental analysis: $C_{21}H_{26}N_2O_3 \cdot HCl$. Calcd.: C, 64.52; H, 6.96; N, 7.17. Found: C, 64.12; H, 6.75; N, 7.05.

NMR spectrum $\delta(d_6\text{-DMSO})$: 1.33(3H, d, J=6 Hz, $CH_3$), 1.70–2.20(4H, m), 2.50–2.85(4H, m), 3.20–3.45(2H, m). 4.85(1H, d, J=9 Hz, $C_1$—H), 7.00(1H, d, J=6 Hz, phenyl protons), 7.40–7.53(6H, m, phenyl protons)

PREPARATION EXAMPLE

An exemplary opthalmologic formula for use of the compound of the present invention as an ophthalmic solution is as follows:

| | |
|---|---|
| Boric acid | 1.8% |
| 1N sodium hydroxide | Suitable amount |
| | Adjusted to pH 7.0 |
| Benzalkonium chloride | 0.005% |
| Trans-2,5-dihydroxy-6-(1-methyl-3-phenylpropylamino)-5,6,7,8-tetrahydro-1-naphthalenecarboxamide hydrochloride | 0.5% |
| Pure water | Suitable amount |
| Total | 100 ml |

TEST EXAMPLE

The intraocular pressure depressant action of trans-2,5-dihydroxy-6-(1-methyl-3-phenylpropylamino)-5,6,7,8-tetrahydro-1-naphthalenecarboxamide hydrochloride [hereinafter referred to briefly as compound (1)] was studied in healthy white rabbits.

50 μl of a 0.5 to 0.05 w/v% solution of compound (1) in physiological saline was instilled into rabbit eyes and the intraocular pressure was measured with a pneumatic applanation tonometer [R. E. Walker et al., Experimental Eye Research 13, 187 (1972)]. The intraocular pressure measurement was carried out immediately before instillation and thereafter repeatedly up to 5.5 hours after instillation and the rate of pressure drop (%) was calculated by means of the following equation: Rate of intraocular pressure drop (%)=

$$\frac{P_0 - P}{P_0 - 9} \times 100$$

[where $P_0$ is the intraocular pressure immediately before instillation, P is the average intraocular pressure after instillation, and the numeral 9 is the value set as the theoretical lower limit of intraocular pressure].

The rate of intraocular pressure drop for each concentration level of compound (1) is given in Table 1.

TABLE 1

| Concentration (w/v %) | $P_0$ (mmHg) | P (mmHg) | Rate of pressure drop (%) | Number of eyes |
|---|---|---|---|---|
| 0.05 | 16.2 ± 1.4 | 14.0 ± 1.3 | 27.6 ± 25.6 | 8 |
| 0.10 | 16.7 ± 1.5 | 13.3 ± 1.9 | 40.3 ± 21.0 | 8 |
| 0.25 | 16.3 ± 1.7 | 13.0 ± 1.5 | 45.4 ± 13.9 | 10 |
| 0.5 | 17.0 ± 2.1 | 11.2 ± 0.6 | 68.7 ± 18.5 | 8 |

What is claimed is:

1. A method of depressing intraocular pressure in a mammal, which comprises administering to the mammal an effective amount of a compound of the formula:

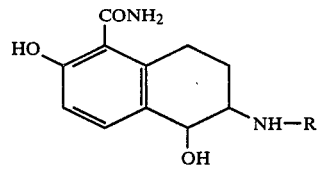

wherein R is phenyl-$C_{1-6}$ alkyl, or a physiologically acceptable salt thereof.

2. A method according to claim 1, wherein the compound or a salt thereof is administered in a local dosage form.

3. A method according to claim 2, wherein the local dosage form is an ophthalmic solution.

* * * * *